United States Patent [19]

Steinberg et al.

[11] Patent Number: 5,151,430
[45] Date of Patent: Sep. 29, 1992

[54] SPECIFIC 17β-THIOBENZOYL-4-AZA-5α-ANDROST-1-EN-3-ONES AS ANTIANDROGEN AGENTS

[75] Inventors: Nathan G. Steinberg, Clark; Gary H. Rasmusson, Watchung; Thomas N. Salzmann, No. Plainfield, all of N.J.

[73] Assignee: Merck & Co., Inc., Rahway, N.J.

[21] Appl. No.: 745,659

[22] Filed: Aug. 16, 1991

Related U.S. Application Data

[63] Continuation of Ser. No. 540,965, Jun. 20, 1990, abandoned.

[51] Int. Cl.⁵ .................. A61K 31/58; C07J 73/00
[52] U.S. Cl. ..................................... 514/284; 546/77
[58] Field of Search ...................... 546/77; 514/284

[56] References Cited

U.S. PATENT DOCUMENTS

| | | | |
|---|---|---|---|
| 2,227,876 | 1/1941 | Bolt | 546/77 |
| 3,239,417 | 3/1966 | Di Tullio et al. | 546/77 X |
| 3,264,301 | 8/1966 | Doorenbos et al. | 546/77 |
| 3,285,918 | 11/1966 | Doorenbos et al. | 544/247 |
| 4,220,775 | 9/1980 | Rasmusson et al. | 546/77 |
| 4,317,817 | 3/1982 | Blohne et al. | 552/518 X |
| 4,377,584 | 3/1983 | Rasmusson et al. | 546/77 X |
| 4,732,897 | 3/1988 | Cainelli et al. | 514/222 |
| 4,760,071 | 7/1988 | Rasmusson et al. | 514/284 |
| 4,845,104 | 7/1989 | Carlin et al. | 514/284 |
| 4,859,681 | 8/1989 | Rasmusson et al. | 514/284 |
| 4,882,319 | 11/1989 | Holt et al. | 514/119 |
| 4,888,336 | 12/1989 | Holt et al. | 514/278 |
| 4,910,226 | 3/1990 | Holt et al. | 514/573 |
| 5,049,562 | 9/1991 | Rasmusson et al. | 514/284 |
| 5,098,908 | 3/1992 | Steinberg et al. | 514/258 |

FOREIGN PATENT DOCUMENTS

| | | | |
|---|---|---|---|
| 970692 | 7/1975 | Canada . | |
| 0004949 | 10/1979 | European Pat. Off. . | |
| 155096 | 9/1985 | European Pat. Off. . | |
| 0271219 | 6/1988 | European Pat. Off. | 546/77 |
| 0277002 | 8/1988 | European Pat. Off. . | |
| 0289327 | 11/1988 | European Pat. Off. . | |
| 0314199 | 5/1989 | European Pat. Off. . | |
| 0343954 | 11/1989 | European Pat. Off. . | |
| 0375344 | 6/1990 | European Pat. Off. . | |
| 0375345 | 6/1990 | European Pat. Off. . | |
| 0375347 | 6/1990 | European Pat. Off. . | |
| 0375349 | 6/1990 | European Pat. Off. . | |
| 1465544 | 11/1965 | France . | |

OTHER PUBLICATIONS

Endo., vol. 91, No. 2 (1972) by Neri, et al., pp. 427–437.
Steroids, 14, 269 (1969), by Nayfeh, et al.
J. Pharm. Sci., 62, 4, pp. 638–640 (1973) by Doorenbos & Solomons.
J. Pharm. Sci., 60, 8, pp. 1234–1235 (1971), by Doorenbos & Brown.
J. Pharm., 63, 4, pp. 620–622 (1974) by Doorenbos & Kim.
J. Med. Chem. (1986) 29 (11): pp. 2298–3115 by Rasmusson, et al.
Prostate (1986) 9 (1): pp. 65–75 by Brooks, et al.
Steroids (1986) 47 (1)° pp. 1–19 by Brooks, et al.
Endocr. (1985) 117 (2): pp. 571–579, by Liang, et al.
J. Med. Chem. (1984) 27 (12)° pp. 1690–1701, by Rasmusson, et al.
J. Org. Chem. (1981) vol. 46, No. 7, pp. 1442–1446.
Chem. Abstracts, vol. 95, 109055j, by T. Liang, et al.
JNCI, vol. 74, No. 2, pp. 475–481 (Feb. 1985), Kadahoma, et al.

(List continued on next page.)

Primary Examiner—Diana G. Rivers
Attorney, Agent, or Firm—Salvatore C. Mitri; Charles M. Caruso

[57] ABSTRACT

Specific 17β-thiobenzoyl-4-aza-5α-androst-1-en-3-ones as antiandrogenic agents of the formula:

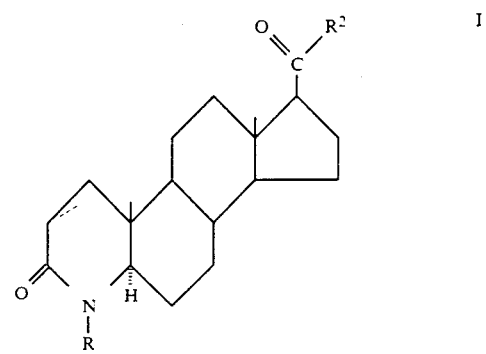

wherein
R is selected from hydrogen, methyl and ethyl and
$R^2$ is phenyl substituted with one or more of: —SH, —S$C_1$—$C_4$ alkyl, —SO—$C_1$—$C_4$ alkyl, —SO$_2$—$C_1$—$C_4$ alkyl, —SO$_2$N—($C_1$-$C_4$ alkyl)$_2$, $C_1$-$C_4$ alkyl, —(CH$_2$)$_m$SH, —S(CH$_2$)$_n$OCOCH$_3$, where m is 1–4, n is 1–3, and providing $C_1$–$C_4$ alkyl is only present when one of the above sulfur-containing radicals is present, wherein the dotted line can represent a double bond, and pharmaceutically acceptable esters and salts thereof. Also included is a pharmaceutical formulation thereof. The above compounds are active as antiandrogenic agents and thus are useful topically for treatment of acne, seborrhea, female hirsutism, and systemically in treatment of benign prostatic hypertrophy.

6 Claims, No Drawings

OTHER PUBLICATIONS

The Prostate, vol. 10, pp. 189-197 (1987) by G. L. Andriole, et al.

J. Endocr., vol. 57, pp. 111-121 (1973), by K. D. Bingham et al.

Toxicol. Appl. Pharmacol., vol. 103, pp. 222-227 (1990), by G. L. Kedderis, et al.

Biorganic Chemistry, 17, pp. 372-376 (1986) by B. W. Metcalf, et al.

Biochemistry, 1990, vol. 29, pp. 2815-2824, by M. A. Levy, et al.

J. Med. Chem., 1990, vol. 33, pp. 943-950, D. A. Holt, et al.

J. Steroid Biochem., vol. 34, Nos. 1-6, pp. 571-575 (1989), by M. A. Levy, et al.

J. Med. Chem. vol. 33, pp. 937-942 (1990) by D. A. Holt, et al.

TIPS, Dec. 1989, vol. 10, pp. 491-495, by D. W. Metcalf, et al.

Prostate, vol. 9, pp. 311-318 (1986) by N. Stone, et al.

Lancet, Nov. 1986, No. 8515, pp. 1095-1096, Labrie, et al.

J. Clin. Endocrin. and Metab., vol. 55, No. 1, pp. 188-193 (1987) Rittmaster, et al.

SPECIFIC 17β-THIOBENZOYL-4-AZA-5α-ANDROST-1-EN-3-ONES AS ANTIANDROGEN AGENTS

This is a continuation, of application Ser. No. 07/540,965, filed Jun. 20, 1990, now abandoned.

BACKGROUND OF THE INVENTION

The present invention relates to specific, new 17β-thiobenzoyl-4-aza-5α-androst-1-en-3-ones and related sulfur-containing compounds and the use of such compounds as antiandrogenic agents.

DESCRIPTION OF THE PRIOR ART

It has been established in the art that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfe et al., Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, an androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

A number of 4-aza steroid compounds are known. See, for example, U.S. Pat. Nos. 2,227,876; 3,239,417; 3,264,301; and 3,285,918; French Pat. No. 1,465,544; Doorenbos and Solomons, J. Pharm. Sci. 62, 4, pp. 638-640 (1973); Doorenbos and Brown, J. Pharm. Sci., 60 8, pp. 1234-1235 (1971); and Doorenbos and Kim, J. Pharm. Sci. 63, 4, pp. 620-622 (1974).

In addition U.S. Pat. Nos. 4,377,584, 4,220,775, 4,859,681, 4,760,071 and the articles J. Med. Chem. 27, p. 1690-1701 (1984) and J. Med. Chem. 29, 2998-2315 (1986) of Rasmusson et al., U.S. Pat. No. 4,845,104 to Carlin et al. and U.S. Pat. No. 4,732,897 to Cainelli et al. describe 4-aza-17β-substituted-5α-androstan-3-ones which are said to be useful in the treatment of hyperandrogenic conditions. However, none of the cited references suggest that 17β-thiobenzoyl-4-aza-5α-androst-1-en-3-ones of the present invention would have utility as highly potent testosterone-5α-reductase inhibitors.

SUMMARY OF THE INVENTION

The present invention is concerned with novel 17β-thiobenzoyl-4-aza-5α-androst-1-en-3-ones and related compounds, processes for their preparation, pharmaceutical formulations comprising the novel compounds as active ingredients and methods of inhibiting testosterone-5α-reductase and of treating hyperandrogenic conditions with the novel compounds or their pharmaceutical formulations.

In accordance with the present invention there is provided compounds of the formula:

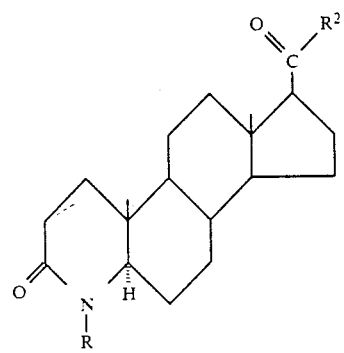

wherein
R is selected from hydrogen, methyl and ethyl and
$R^2$ is phenyl substituted with one or more of: —SH, —S$C_1$–$C_4$ alkyl, —SO$C_1$–$C_4$ alkyl, —SO$_2$—$C_1$–$C_4$ alkyl, —SO$_2$N($C_1$–$C_4$ alkyl)$_2$, $C_1$–$C_4$ alkyl, —(CH$_2$)$_m$SH, S—(CH$_2$)$_n$OCOCH$_3$, where m is 1–4, n is 1–3, and providing $C_1$–$C_4$-alkyl is only present when one of the above sulfur containing radicals is present, wherein the dotted line can represent a double bond, and pharmaceutically acceptable esters and salts thereof.

Preferred embodiments of the novel 17β-acyl compounds of our invention are represented by the formula:

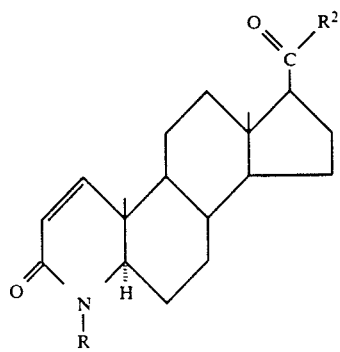

wherein

R is hydrogen, methyl or ethyl, and

R² is phenyl substituted with one or more sulfur-containing groups as described herein on the 2, 3, 4 or 5 positions of the phenyl ring.

Representative compounds of the present invention include the following:

17β-(4-thiophenylcarbonyl)-4-aza-5α-androst-1-en-3-one;

17β-(3-thiophenylcarbonyl)-4-aza-5α-androst-1-en-3-one;

17β-(4-methylthiophenylcarbonyl)-4-aza-5α-androst-1-en-3-one;

17β-(4-methylsulfinylphenylcarbonyl)-4-aza-5α-androst-1-en-3-one;

17β-(4-methylsulfophenylcarbonyl)-4-aza-5α-androst-1-en-3-one;

17β-(3-methylsulfinylphenylcarbonyl)-4-aza-5α-androst-1-en-3-one;

17β-(4-N,N-dimethylaminosulfophenylcarbonyl)-4-aza-5α-androst-1-en-3-one;

17β-(2-ethyl-4-methylthiophenylcarbonyl)-4-aza-5α-androst-1-en-3-one;

17β-(4-thioethylphenylcarbonyl)-4-aza-4-methyl-5α-androst-1-en-3-one;

17β-(4-acetoxymethylthiophenylcarbonyl)-4-aza-4-methyl-5α-androst-1-en-3-one;

17β-(2-methyl-4-methylthiophenylcarbonyl)-4-aza-4-methyl-5α-androst-1-en-3-one;

17β-(2-methyl-4-methylsulfinylphenylcarbonyl)-4-aza-4-methyl-5α-androst-1-en-3-one;

17β-(2-isopropyl-4-methylsulfophenylcarbonyl)-4-aza-4-methyl-5α-androst-1-en-3-one;

17β-(4-methylthiophenylcarbonyl)-4-aza-4-methyl-5α-androstan-3-one;

17β-(4-methylsulfinylphenylcarbonyl)-4-aza-4-methyl-5α-androstan-3-one;

17β-(4-methylsulfophenylcarbonyl)-4-aza-4-methyl-5α-androstan-3-one; and the like, and the corresponding compounds wherein the 4-hydrogen substituent is replaced in each of the above named compounds by a methyl or an ethyl radical.

Also included within the scope of this invention are pharmaceutically acceptable salts or esters, where a basic or acidic group is present on the thiobenzoyl moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl and the like, and those esters known in the art for modifying solubility or hydrolysis characteristcs for use as sustained release or prodrug formulations.

The novel compounds of formula I of the present invention are prepared by a method starting with the known steroid ester of the formula:

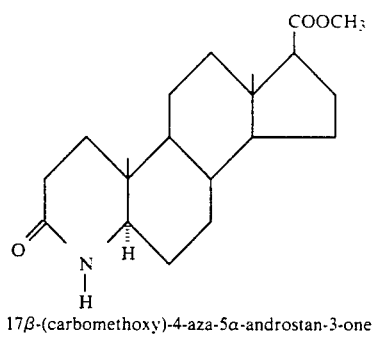

17β-(carbomethoxy)-4-aza-5α-androstan-3-one which includes the stages of (1) dehydrogenating said starting material to produce the corresponding compound containing a double bond in the 1,2-position of the A-ring, (2) converting the 17-carbomethoxy substituent into a 17β-acyl substituent and, if desired (3) alkylating the A-ring nitrogen to introduce 4-methyl or 4-ethyl substituents into the A-ring. For the dehydrogenation step, it is preferable that the 4-aza nitrogen be unsubstituted. The dehydrogenation step can be carried out, e.g. according to the procedure of Dolling, et al, involving dichlorodicyanobenzoquinone, JACS (1988) Vol. 110, pp. 3318–3319. Stage (2) may consist of one or more chemical steps and if desired may take place before stage (1) or following stage (1) or stage (3).

In accordance with the process of the present invention, the products of our invention are formed by (1) heating a 17β-alkoxycarbonyl-4-aza-5α-androstan-3-one compound III with a dehydrogenating agent such as benzeneseleninic anhydride in refluxing chlorobenzene to form a 17β-alkoxycarbonyl-4-aza-5α-androst-1-en-3-one (IV), (2) the formed 5α-androst-1-en-3-one compound from step (1) is reacted with sodium hydride and under anhydrous conditions in a neutral solvent such as dimethylformamide, (2) contacting the resulting reaction mixture with an alkyl (methyl or ethyl) iodide to form the corresponding 17β-alkoxycarbonyl-4-alkyl-4-aza-5α-androst-1-en-3-one (V), (3) subsequently hydrolyzing said 17β-alkoxycarbonyl-4-alkyl-4-aza-5α-androst-1-en-3-one with a strong base such as aqueous methanolic potassium hydroxide at the reflux temperature, followed by acidification and isolation of the resulting steroidal acid, 17β-carboxy-4-alkyl-4-aza-5α-androst-1-en-3-one (VI), (4) said steroidal acid is then converted to its corresponding 2-thiopyridyl ester by refluxing with triphenyl phosphine and 2,2'-dipyridyl disulfide in an inert solvent and the product 17β-(2-pyridylthiocarbonyl)-4-alkyl-4-aza-5α-androst-1-en-3-one (VII) is isolated by chromatography on silica, (5) said pyridylthio ester is then reacted with an R²-Li or an R²MgX (X=Cl, Br) Grignard reagent such as p-methyl-thiophenyl-magnesium chloride in tetrahydrofuran to form the desired product 17β-(p-methylthiophenyl-carbonyl)-4-alkyl-4-aza-5α-androst-1-en-3-one (VIII) which is isolated by chromatography on silica gel.

When this reaction is carried out using an R²MgX or R²-Li compound in place of p-methylthiophenyl magnesium chloride, the corresponding 17β-(substituted benzoyl)-4-alkyl-4-aza-5α-androst-1-en-3-one is prepared wherein phenyl is R².

The Grignard reagent, R²MgX, for all the species included within the scope of this invention, are available and can readily be made by one skilled in the art. For example, where R² is $C_1$-$C_4$ alkyl thiophenyl, can be formed from the appropriate $C_1$-$C_4$ alkyl thiobromobenzene, e.g. p-methylthiobromobenzene.

The formed $C_1$-$C_4$ alkyl thiobenzene can be used to further prepare $C_1$-$C_4$ alkyl sulfoxides for oxidation with e.g. m-chloroperbenzoic acid. The resulting sulfoxide can be further oxidized by the use of the m-chloroperbenzoic acid reaction to proceed for a longer period of time to form the $C_1$-$C_4$ alkyl sulfone.

Further, the sulfoxide can be used in the Pummerer rearrangement to form the corresponding thiol.

The —$SO_2N(C_1$-$C_4$ alkyl$)_2$ substituted phenyl ($R^2$) is formed from the appropriate bromobenzene, e.g. p-N,N-dimethylaminosulfobromobenzene which is used directly in the Grignard reaction to form the final product.

The thioalkyl groups on the phenyl ring, i.e. —$(CH_2)_mSH$, where m is 1-4, are readily formed via a four step procedure from an alkoxy alkyl phenyl bromide, Br—$C_6H_4$—$(CH_2)_mOCH_3$. Direct addition of the Grignard reagent prepared from above-bromoalkyl phenyl derivative to the thiopyridyl ester results in the keto derivative, i.e. 17β(4 methoxyl alkyl benzoyl)-4-aza-5α-androst-1-ene-3-one. This can be readily converted into thio analogue via $BBr_3$ at $-70°$ C. to form the hydroxyalkyl derivative, followed by displacement by halogen, e.g. bromo and then converting the halogenated compound through NaSH displacement to give the final mercapto compound.

In accordance with the process of our invention, the corresponding 17β-substituted thiobenzoyl-4-aza-5α-androst-1-en-3-one XV is readily prepared from the 17β(alkoxycarbonyl)-4-aza-5α-androsten-3-one (IV) by repeating the above series of reaction steps but omitting step 2 hereinabove, i.e., treatment of the 4-aza-5α-androst-1-en-3-one with sodium amide followed by methyl or ethyl iodide.

In accordance with a further alternate process of preparing the compounds of our invention, having only hydrogen as the sole substituent on the ring A-nitrogen, the double bond in the A-ring is introduced as the last step of the process. Thus, a 17β-alkoxycarbonyl-4-aza-5α-androstan-3-one (III) is hydrolyzed to the corresponding steroidal acid, 17β-carboxy-4-aza-5α-androstan-3-one, (IX) which, in turn, is converted to the corresponding thio-pyridyl ester, 17β-(2-pyridylthiocarbonyl)-4-aza-5α-androstan-1-one (X) followed by treatment of the ester with an $R^2MgX$ or $R^2Li$ compound wherein $R^2$ is as defined hereinabove to form a 17β-(substituted thiobenzoyl)-4-aza-5α-androstan-3-one (XI) which is dehydrogenated as previously described to produce compound XIV, 17β-(acyl)-4-aza-5α-androstan-1-en-3-one.

The above reactions are schematically represented in the following structural outline:

Flowsheet

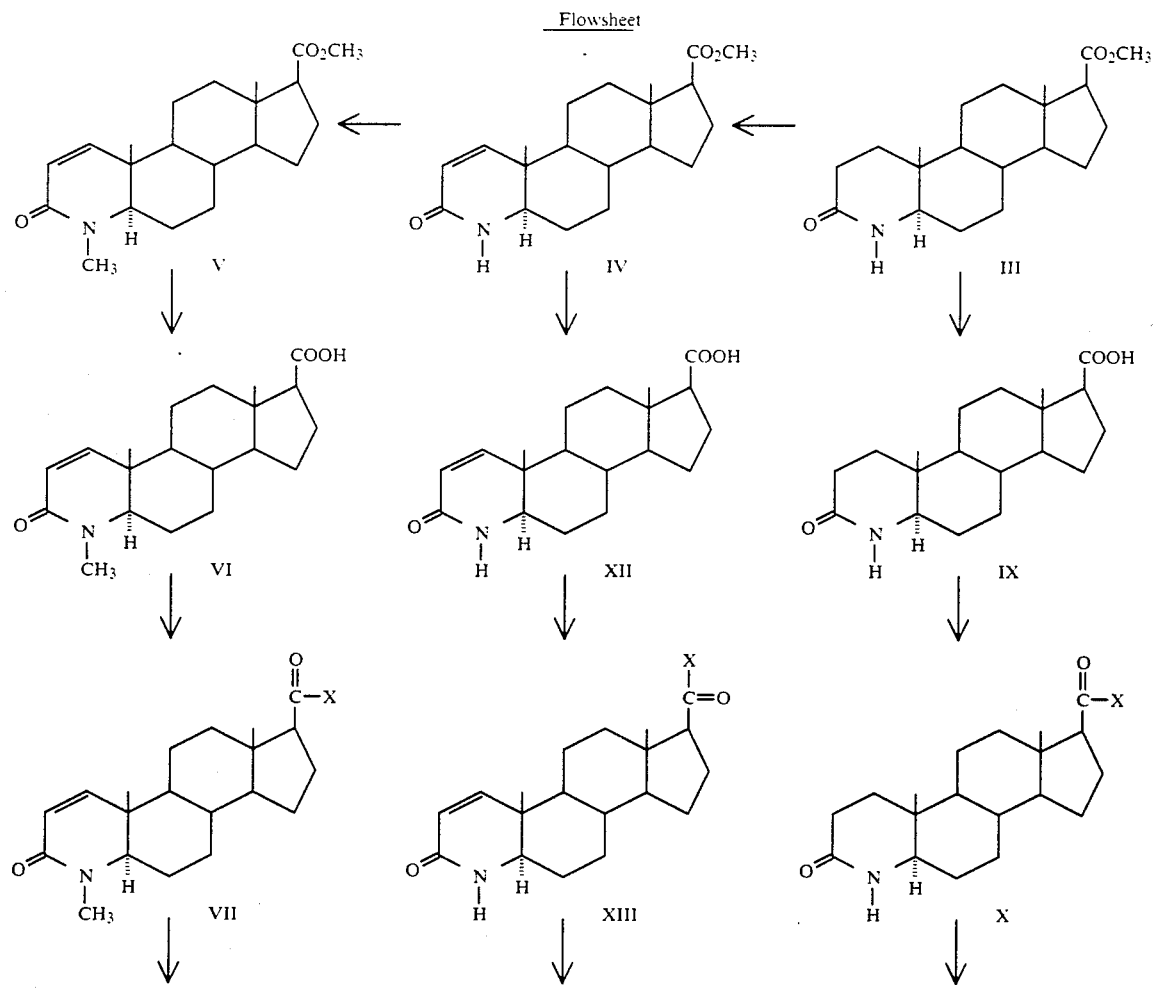

-continued
Flowsheet

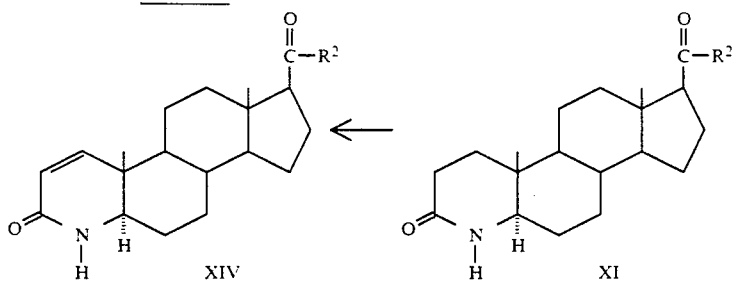

X is 2-pyridylthio
R² substituted thiophenyl wherein X is a 2-pyridylthiocarbonyl substituent and R² is defined as hereinabove.

The compounds of the present invention, prepared in accordance with the method described above, are, as already described, potent antiandrogens by virtue of their ability to specifically inhibit testosterone-5α-reductase.

Also within the scope of the present invention are ketone reduction products of I, the secondary alcohols of the formula:

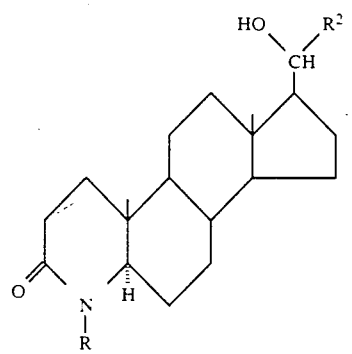

wherein

R is selected from hydrogen, methyl and ethyl and

R² is phenyl substituted with one or more of: —SH, —SC₁-C₄ alkyl, —SOC₁-C₄ alkyl, —SO₂—C₁-C₄ alkyl, —SO₂N(C₁-C₄ alkyl)₂, C₁-C₄ alkyl, C₁-C₄ alkyl, —(CH₂)$_m$SH, —S(CH₂)$_n$OCOCH₃, where m is 1-4, n is 1-3, and providing C₁-C₄ alkyl is only present when one of the above sulfur-containing radicals is present, wherein the dotted line can represent a double bond, and pharmaceutically acceptable esters and salts thereof.

These compounds can be made by conventional sodium borohydride reduction of the carbonyl attached to R² without reducing the amide carbonyl in Ring A or the 1,2-double bond if present. If the R² phenyl contains a carbonyl function, it can be selectively blocked and then regenerated after the borohydride reduction by conventional methods. The borohydride reduction can be carried out in, e.g. water or aqueous methanol, at a temperature of room temperature to 50° C. and the product then isolated and purified by conventional means. The compounds are also active as 5-α reductase inhibitors.

Accordingly, the present invention is particularly concerned with providing a method of treating the hyperandrogenic conditions of acne vulgaris, seborrhea, and female hirsutism by topical administration, and a method of treating all of the above conditions as well as benign prostatic hypertrophy, by oral or parenteral administration, of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of acne vulgaris, seborrhea, female hirsutism, the compounds of the present invention are administered in the formula of pharmaceutical composition comprising the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The method of preparing the novel 17$\beta$-N-monosubstituted or 17$\beta$ acyl carbamoyl compounds of the present invention, already described above in general terms, may be further illustrated by the following examples.

EXAMPLE 1

Methyl 3-oxo-4-aza-5$\alpha$-androst-1-ene-17$\beta$-carboxylate

A suspension of 83.7 g of methyl 3-oxo-4-aza-5$\alpha$-androstane-17-carboxylate* and 126.5 g of benzeneseleninic anhydride in 2.09 l of chlorobenzene was heated at reflux for 2 hours. The reflux condenser was switched to a distillation head and the mixture was distilled slowly to remove water that had formed in the reaction (2 hours). The solution was evaporated to leave 198 g of wet residue. The residue as a solution in dichloromethane was washed with saturated aqueous $NaHCO_3$ solution and saturated NaCl solution, then dried and evaporated to leave 172.4 g. This material was chromatographed on 2.56 kg of silica gel eluting first with dichloromethane (5 liters) and then with 4:1 dichloromethaneacetone. The desired product was eluted with 8 liters of the above-mixed solvent, evaporated in vacuo to yield 53.4 g of solid. It was washed with diethyl ether and dried to leave 49.5 g of the above-titled compound, m.p. 278°–280° C.

*Rasmusson Johnston and Arth. U.S. Pat. No. 4,377,584, Mar. 22, 1983.

EXAMPLE 2

S-(2-Pyridyl)-3-oxo-4-aza-5$\alpha$-androst-1-ene-17$\beta$-thiocarboxylate

A suspension of 25 g of the product of Example 1 in 125 ml of methanol was treated with a solution of KOH (*12.5 g) in 12.5 ml of water. After refluxing for 4 hours, the solution was acidified with 6N HCl and then was diluted with water. The crude acid (23.32 g) was separated, dried and had m.p. 300° C.

The crude, dry acid (23 g), triphenylphosphine (36.45 g) and 2,2'-dipyridyldisulfide (30.4 g) were suspended in 138 ml of toluene with stirring for 3 hours at room temperature. The reaction mixture was directly chromatographed on a column of 4.5 kg of silica gel eluting with 9:1 ethyl acetate-acetone to give 20.4 g of the desired product, m.p. 218°–220° C.

EXAMPLE 3

Synthesis of
17-$\beta$-(4-Methylthiobenzoyl)-4-aza-5-$\alpha$-androst-1-en-3-one To a suspension of 250.0 mg of dry activated magnesium chips in 8.0 ml of dry THF was added 810.0 mg of p-bromophenyl methyl sulfide in 2.0 ml of dry THF under $N_2$. The reaction was run in an ultrasonic bath at a temperature range of 24°–30° C. To the well-agitated mixture was added dropwise 40 $\mu$l of 1,2-dibromoethane/$N_2$. The reaction was allowed to proceed for 1 to 1$\frac{1}{2}$ hours at 28° C./$N_2$. The concentration of the Grignard reagent was 4.0 mmoles in 10 ml of dry THF.

The steroid from Example 2, i.e. the pyridylthio ester, 205 mg, was suspended in 2.0 ml of dry THF, cooled to −80° C. and the above Grignard (3.79 ml; 3 equivalents) was added via syringe to the steroidal suspension in 5–10 minutes/$N_2$. The reaction was allowed to proceed for 1 hour at −80° C./$N_2$ and then at −10° C. for an additional hour/$N_2$. The solution was diluted with 10.0 ml of methylene chloride, and quenched with saturated aqueous solution of $NH_4Cl$ to pH=4. The organic layers were separated, washed 3 times with water; 3 times with saturated sodium chloride, dried over $MgSO_4$, filtered, and evaporated under vacuum to afford 110.0 mg of crude product.

The crude product was chromatographed on TLC (one plate, 20 cm × 20 cm × 20 cm × 1000 $\mu$m silica gel) eluted with 80:20 ($CH_2Cl_2$-acetone) to afford 66.0 mg of single spot material. Crystallization from EtOAc afforded 45.0 mg of the above-titled compound, m.pt. 286°–287° C.

FAB for $C_{26}H_{33}NO_2S$ (Calcd.) 424; Found 424.

EXAMPLE 4

Synthesis of
17-$\beta$-(4-methylsulfinylbenzoyl)-4-aza-5$\alpha$-androst-1-en-3-one

A. Oxidation 19.91 mg of the methylthio product from Example 3 was dissolved in 2.5 ml of $CH_2Cl_2$, cooled to 0°–(−2)° C. and added via syringe 9.6 mg of m-chloroperbenzoic acid in 1.0 ml of $CH_2Cl_2$ over a period of 4 minutes. After stirring for 1 hour at 0°–(−2)° C., the reaction was diluted with 10 ml. $CH_2Cl_2$. The layers were washed subsequently with 2.5% $NaHCO_3$, $H_2O$ and saturated NaCl solutions. The organic layer was dried over $MgSO_4$ overnight, filtered and evaporated in vacuo to yield 17 mg product. Crystallization from EtOAc gave 11.8 mg of the above-titled compound, a solid, mp. 313°–313.5° C. (with dec.).

Anal. Calcd. for $C_{26}H_{33}NO_3S \cdot \frac{1}{2}H_2O$: C,70.31; H,7.60; N, 3.15;
Found: C,70.47; H,7.70; N,3.00.
FAB for $C_{26}H_{33}NO_3S$ (Calcd. 440); Found 440.

Sulfone

Fifteen percent (15%) of the corresponding sulfone, 17$\beta$-(4-methylsulfonyl benzoyl) derivative, was isolated by chromatography from the reaction as a byproduct. Recrystallized from EtOAc to yield a solid, mp. 279°–279.5° C. Molecular weight by FAB showed 456; calculated 456.

Anal. for $C_{26}H_{33}NO_4S \cdot 0.25\ H_2O$ Calc: C,67.87; H,7.28; N,3.04. Found: C,67.96; H,6.72; N,2.95.

EXAMPLE 5

Synthesis of
17-$\beta$-(4-acetoxymethylthiobenzoyl)-4-aza-5$\alpha$-androst-1-en-3-one

A. Pummerer Rearrangement

Trifluoroacetic anhydride (165 $\mu$l) was dissolved in 780 $\mu$l of acetic anhydride and kept for 5 hours at room temperature (RT).

To 300 $\mu$l of the above solution of mixed anhydrides was added 34.15 mg pure sulfoxide from Example 4 with stirring. A few minutes later 54.0 $\mu$l of 2,6-lutidine was added and the reaction was allowed to stir at RT/$N_2$ for 17 hours.

The liquid anhydrides were removed under reduced pressure and the remaining solution extracted (4 times with $CHCl_3$). The $CHCl_3$ extracts were washed subsequently with dilute HCl; 5% $NaHCO_3$ solution, 3 times; 3 times with $H_2O$; and finally with saturated NaCl solution, and then dried over $MgSO_4$ filtered and evaporated the solution to dryness in vacuo to yield 42.1 mg of crude product.

Purification

The crude product from Step A was purified by chromatography on silica gel using 95:5 ($CHCl_3$-acetone) as eluant and then crystallizing the obtained solid from EtOAc to yield 17.8 mg of the above-titled compound as crystals, m.pt. 235°–236° C. (dec.)

Anal. Calcd. for $C_{28}H_{35}O_4NS \cdot \frac{1}{4} H_2O$: C,68.57; H,7.40; N,2.86; Found: C,69.02; H,7.39; N,2.73.

FAB for $C_{28}H_{28}O_4NS$ calcd.: 482; Found 482.

The NMR (proton) was in excellent agreement with the proposed product structure.

EXAMPLE 6

Synthesis of 17β(4-mercaptobenzoyl)-4-aza-5α-androst-1-en-3 one 40.0 mg of the acetoxy-methyl-thio derivative from Example 5 was suspended in 3.0 ml of isopropanol. The reaction mixture was flushed several times with $N_2$, and with vacuum, and the system kept under nitrogen atmosphere. To the above mixture was added 40.0 mg of $K_2CO_3$ in 2.00 ml of water (free of oxygen) via syringe, and the tempeature of the reaction mixture was allowed to rise to 80° C. under gentle reflux under slight vacuum for 10 minutes, and then under $N_2$ for 1 hour. After 1 hour, the reaction mixture was a clear yellow solution. It was brought to R.T., cooled to 0°–5° C. and quenched with 2.5N HCl acid/$N_2$. The reaction mixture was extracted 4 times with $CH_2Cl_2$. The organic layer was washed with $H_2O$ 4 times; 3 times with saturated salt solution, and finally dried over $MgSO_4$. Filtered and evaporated to dryness in vacuo to yield 36.9 mg of crude product. The crude product was dissolved in 2.0 ml of $CHCl_3$, filtered through Teflon (Acrodisc CR) and purified by preparative HPLC (Waters Prep peak) on silica gel and eluted with 60:40 ($CH_2Cl_2$-acetone). Crystallization, from EtOAc afforded a single spot material, 20.7 mg of the above-titled compound, m.pt. 285°–286° C.

Anal. Calcd. for $C_{25}H_{31}O_2NS \cdot \frac{1}{2} H_2O$: C,72.19; H,7.69; N,3.24; Found: C,71.82; H,7.43; N,3.26.

FAB: Calcd. for $C_{25}H_{31}O_2NS$: 410; Found: 410.

What is claimed is:

1. A compound of formula:

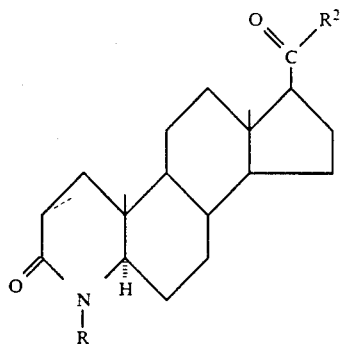

I wherein

R is selected from hydrogen, methyl and ethyl and
$R^2$ is phenyl substituted with one or more of: —S$C_1$-$C_4$ alkyl, —SO$C_1$-$C_4$ alkyl, —SO$_2C_1$-$C_4$ alkyl, —SO$_2$N($C_1$-$C_4$- alkyl)$_2$, $C_1$-$C_4$ alkyl, —(CH$_2$)$_m$SH, —S—(CH$_2$)$_n$—O—COCH$_3$, where m is 1-4, n is 1-3, providing $C_1$-$C_4$ alkyl is only present when one of the above sulfur-containing radicals is present, wherein the dotted line can represent a double bond, and pharmaceutically acceptable esters and salts thereof.

2. The compound of claim 1 wherein:
R is hydrogen, methyl or ethyl and
$R^2$ is methylthiophenyl, methylsulfinyl-phenyl, methylsulfophenyl, aminosulfophenyl, thioethylphenyl or acetoxymethylthiophenyl.

3. The compound of claim 1 which is a member selected from the group:

17β-(4-methylthiophenylcarbonyl)-4-aza-5α-androst-1-en-3-one;
17β-(4-methylsulfinylphenylcarbonyl)-4-aza-5α-androst-1-en-3-one;
17β-(4-methylsulfophenylcarbonyl)-4-aza-5α-androst-1-en-3-one;
17β-(3-methylsulfinylphenylcarbonyl)-4-aza-5α-androst-1-en-3-one;
17β-(4-N,N-dimethylaminosulfophenylcarbonyl)-4-aza-5α-androst-1-en-3-one;
17β-(2-ethyl-4-methylthiophenylcarbonyl)-4-aza-5α-androst-1-en-3-one;
17β-(4-thioethylphenylcarbonyl)-4-aza-5α-androst-1-en-3-one;
17β-(4-acetoxymethylthiophenylcarbonyl)-4-aza-4-methyl-5α-androst-1-en-3-one;
17β-(2-methyl-4-methylthiophenylcarbonyl)-4-aza-4-methyl-5α-androst-1-en-3-one;
17β-(2-methyl-4-methylsulfinylphenylcarbonyl)-4-aza-4-methyl-5α-androst-1-en-3-one;
17β-(2-isopropyl-4-methylsulfophenylcarbonyl)-4-aza-4-methyl-5α-androst-1-en-3-one;
17β-(4-methylthiophenylcarbonyl)-4-aza-4-methyl-5α-androstan-3-one;
17β-(4-methylsulfinylphenylcarbonyl)-4-aza-4-methyl-5α-androstan-3-one; or
17β-(4-methylsulfophenylcarbonyl)-4-aza-4-methyl-5α-androstan-3-one.

4. A method of treating the hyperandrogenic condition of acne vulgaris, seborrhea, female hirsutism, and benign prostatic hypertrophy comprising parenteral administration to a patient in need of such treatment of a therapeutically effective amount of a compound of formula:

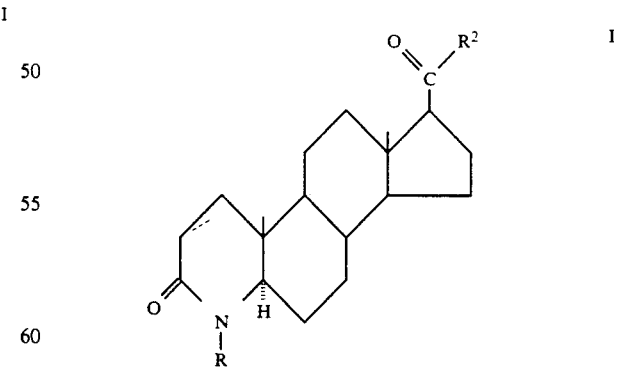

I wherein

R is selected from hydrogen, methyl and ethyl, and
$R^2$ is phenyl substituted with one or more of: —S$C_1$-$C_4$ alkyl, —SO$C_1$-$C_4$ alkyl, —SO$_2C_1$-$C_4$ alkyl, —SO$_2$N($C_1$-$C_4$-alkyl)$_2$, $C_1$-$C_4$ alkyl, —(CH$_2$)$_m$SH, —S—(CH$_2$)$_n$—OCOCH$_3$, where m is 1-4, n is 1-3, providing $C_1$-$C_4$ alkyl is only present when one of the above sulfur-containing radicals is present, wherein the dotted line can represent a double bond, and pharmaceutically acceptable esters and salts thereof.

5. A pharmaceutical composition comprising a pharmaceutically acceptable carrier and a therapeutically effective amount of a compound according to claim 1.

6. A compound of the formula:

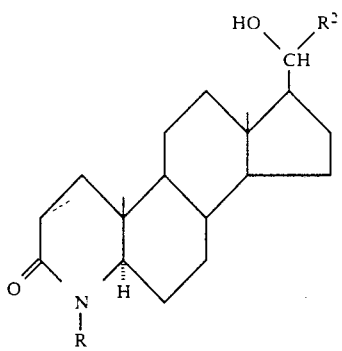

wherein
R is selected from hydrogen, methyl and ethyl, and
$R^2$ is phenyl substituted with one or more of: $-SC_1$-$C_4$ alkyl, $-SOC_1$-$C_4$ alkyl, $-SO_2C_1$-$C_4$ alkyl, $-SO_2N(C_1$-$C_4$-alkyl$)_2$, $C_1$-$C_4$ alkyl, $-(CH_2)_m SH$, $-S-(CH_2)_n-OCOCH_3$, where m is 1-4, n is 1-3, and providing $C_1$-$C_4$ alkyl is only present when one of the above sulfur-containing radicals is present, wherein the dotted line can represent a double bond, and pharmaceutically acceptable esters and salts thereof.

* * * * *